United States Patent [19]
Guo et al.

[11] Patent Number: 5,972,379
[45] Date of Patent: Oct. 26, 1999

[54] LIPOSOME COMPOSITION AND METHOD FOR ADMINISTERING A QUINOLONE

[75] Inventors: Luke S. S. Guo, Lafayette; Josh Gittelman; Samuel Zalipsky, both of Redwood City; Francis J. Martin, San Francisco, all of Calif.

[73] Assignee: Sequus Pharmaceuticals, Inc., Menlo Park, Calif.

[21] Appl. No.: 09/054,857

[22] Filed: Apr. 2, 1998

Related U.S. Application Data

[63] Continuation-in-part of application No. 08/866,455, May 30, 1997, abandoned, which is a continuation of application No. 08/388,374, Feb. 14, 1995, abandoned.

[51] Int. Cl.⁶ ................................................ A61K 9/127
[52] U.S. Cl. ........................................ 424/450; 264/4.1
[58] Field of Search .............................. 424/450; 264/4.1, 264/4.3

[56] References Cited

U.S. PATENT DOCUMENTS

| | | | |
|---|---|---|---|
| 4,772,594 | 9/1988 | Hashimoto | 514/178 |
| 5,057,523 | 10/1991 | Chu et al. . | |
| 5,077,056 | 12/1991 | Bally et al. . | |
| 5,192,549 | 3/1993 | Barenolz et al. . | |
| 5,380,531 | 1/1995 | Chakrabarti et al. . | |
| 5,741,516 | 4/1998 | Webb | 424/450 |
| 5,785,987 | 7/1998 | Hope | 424/450 |

FOREIGN PATENT DOCUMENTS

| | | |
|---|---|---|
| 0652 008 | 5/1995 | European Pat. Off. . |
| WO 91/09616 | 7/1991 | WIPO . |
| WO 96/25147 | 8/1996 | WIPO . |
| WO 96/26715 | 9/1996 | WIPO . |

OTHER PUBLICATIONS

Agarwel in J. Med. Chem 33, p. 1505 (1990).
Boman, N.L. et al., "Optimization of the Retention Properties of Vincristine in Liposomal Systems," *Biochimica et Biophysica Acta*. 1152: 253–258 (1993).
Brossi, A. et al., "1–Ethyl–7–[3–[(ethylamino)methyl]–1–pyrrolidinyl]–6,8–difluoro–1, 4–dihydro–4–oxo–3–quinoline–carboxylic Acid. New Quinolone Antibacterial with Potent Gram–Positive Activity," *J. Med. Chem.* 29: 445–448 (1986).
Culbertson, T.P. et al., "Quinolone Antibacterial Agents Substituted at the 7–Position with Spiroamines. Synthesis and Structure–Activity Relationships," *J. Med. Chem.* 33: 2270–2275 (1990).
Hagen, S.E. et al., "New Quinolone Antibacterial Agents. Synthesis and Biological Activity of 7–(3,3–or 3,4–Disubstituted–1–pyrrolidinyl)quinoline–3–carboxylic Acids," *J. Med. Chem.* 33: 849–854 (1990).
Hagen, S.E. et al., "Synthesis and Biological Activity of 5–Alkyl–1,7,8,–trisubstituted–6–fluoroquinoline–3–carboxylic Acids," *J. Med. Chem.* 34: 1155–1161 (1991).
Klopman, G. et al., "Anti–*Mycobacterium avium* Activity of Quinolones: In Vitro Activities," *Antimicrobial Agents and Chemotherapy.* 37:(09) 1799–1806 (1993).
Lasic, D.D. et al., "Gelation of Liposome Interior," *FEBS.* 312:(02,03) 255–258 (1992).
Madden, T.D. et al., "The Accumulation of Drugs within Large Unilamellar Vesicles Exhibiting a Proton Gradient: A Survey," *Chemistry and Physics of Lipids* 53: 37–46 (1990).
Renau, T.E. et al., "Structure—Activity Relationships of the Quinolone Antibacterials against Mycobacteria: Effect of Structural Changes at N–1 and C–7," *J. Med. Chem.* 39: 729–735 (1996).
Sanchez J.P. et al., "Quinolone Antibacterial Agents. Synthesis and Structure—Activity Relationships of 8–Substituted Quinoline–3–carboxylic Acids and 1,8–Naphthyridine–3–carboxylic Acids," *J. Med. Chem.* 31: 983–991 (1988).

*Primary Examiner*—Gollamudi S. Kishore
*Attorney, Agent, or Firm*—Judy M. Mohr; Dehlinger & Associates

[57] ABSTRACT

A liposome composition for treating a bacterial infection is described. The composition includes liposomes having a surface coating of hydrophilic polymer chains and an entrapped drug-conjugate composed of ciprofloxacin conjugated to an amino acid.

10 Claims, 6 Drawing Sheets

LIPOSOME COMPOSITION AND METHOD FOR ADMINISTERING A QUINOLONE

This application is a continuation-in-part application of pending application Ser. No. 08/866,455, filed May 30, 1997 now abandoned, which is a continuation of application Ser. No. 08/388,374, filed Feb. 14, 1995, now abandoned. Both applications are incorporated herein by reference.

FIELD OF THE INVENTION

The present invention relates to a composition for administration of a quinolone for treatment of a bacterial infection, and more particularly to a liposome composition for administration of a drug-conjugate of ciprofloxacin covalently attached to an amino acid.

REFERENCES

Chakrabarti, A., et al., U.S. Pat. No. 5,380,532, issued Jan. 10, 1995.

Cramer, J., et al., *Biochemical and Biophysical Research Communications* 75(2):295–301 (1977).

Culbertson, T. P., et al., *J. Med. Chem.* 33:2270–2275 (1990).

Deamer, D. W., et al., *Biochim. et Biophys. Acta* 274:323 (1972).

Domagala, J. M., et al., *J. Med. Chem.* 29:448–453 (1986).

Greene, T. W., et al., *PROTECTIVE GROUPS IN ORGANIC SYNTHESIS*, 2nd ed., John Wiley & Sons, New York, N.Y. (1991).

Hagen, S. E., et al., *J. Med. Chem.* 33:849–854 (1990).

Hagen, S. E., et al., *J. Med. Chem.* 34:1155–1161 (1991).

Hope, M., et al., WO 96/26715, "METHOD FOR LOADING LIPID VESICLES", published Sep. 6, 1996.

Klopman, G. et al., *Antimicrobial Agents and Chemotherapy*, Sept.:1807–1815 (1993).

Lehninger, A. L., PRINCIPLES OF BIOCHEMISTRY, Worth Publishers, 1982.

Madden, T. D., et al., *Chemistry and Physics of Lipids* 53:37–46 (1990).

Martin, F. J., In: *SPECIALIZED DRUG DELIVERY SYSTEMS-MANUFACTURING AND PRODUCTION TECHNOLOGY*, (P. Tyle, ed.) Marcel Dekker, New York, pp. 267–316 (1990).

Nichols, J. W., et al., *Biochim. Biophys. Acta* 455:269–271 (1976).

Paphadjopoulos, D. et al., *Proc. Natl. Acad. Sci. U.S.A.*, 88:11460–11464 (1991).

Ryan, J., et al., WO 91/09616, "QUINOLONE ANTIBIOTICS ENCAPSULATED IN LIPID VESICLES", published Jul. 11, 1991.

Sanchez, J. P. et al., *J. Med. Chem.* 31:983–991 (1988).

Salyers, A. A. and Whitt, D. D., *BACTERIAL PATHOGENESIS, A MOLECULAR APPROACH*, ASM Press, Washington D.C., 1994, p. 101–102.

Szoka, F., Jr., et al., *Ann. Rev. Biophys. Bioeng.* 9:467 (1980).

Wong, J. P. et al., European Patent Application 0 652 008 entitled "LIPOSOME-ENCAPSULATED CIPROFLOXACIN", published May 10, 1995.

Zalipsky, S., in STEALTH LIPOSOMES, D. Lasic and F. Martin, Eds., CRC Press, Chapter 9 (1995).

BACKGROUND OF THE INVENTION

Liposomes have been proposed as carriers for a variety of therapeutic agents. Drug delivery systems utilizing liposomes offer the potential of improved delivery properties, including enhanced blood circulation time, reduced cytotoxicity, sustained drug release, and targeting to selected tissues.

In utilizing liposomes for drug delivery, it is generally desirable to load the liposomes to high encapsulated drug concentration. Rate of leakage of the drug from the liposomes should also be low, to preserve the advantages of drug delivery in liposome-entrapped form.

A variety of drug-loading methods are available for preparing liposomes with entrapped drug. In the case of many lipophilic drugs, efficient drug entrapment can be achieved by preparing a mixture of vesicle-forming lipids and the drug, e.g., in a dried film, and hydrating the mixture to form liposomes with drug entrapped predominantly in the lipid bilayer phase of the vesicles. Assuming the partition coefficient of the drug favors the lipid phase, high loading efficiency and stable drug retention can be achieved.

The same type of passive loading may also be employed for preparing liposomes with encapsulated hydrophilic compounds. In this case, the drug is usually dissolved in the aqueous medium used to hydrate a lipid film of vesicle-forming lipids. Depending on the hydration conditions, and the nature of the drug, encapsulation efficiencies of between about 5–20% are typically obtained, with the remainder of the drug being in the bulk aqueous phase. An additional processing step for removing non-encapsulated drug is usually required.

A more efficient method for encapsulated hydrophilic drugs, involving reverse evaporation from an organic solvent, has also been reported (Szoka, et al., 1980). In this approach, a mixture of hydrophilic drug and vesicle-forming lipids are emulsified in a water-in-oil emulsion, followed by solvent removal to form an unstable lipid-monolayer gel. When the gel is agitated, typically in the presence of added aqueous phase, the gel collapses to form oligolamellar liposomes with high (up to 50%) encapsulation of the drug.

In the case of ionizable hydrophilic or amphipathic drugs, even greater drug-loading efficiency can be achieved by loading the drug into liposomes against a transmembrane ion gradient (Nichols, et al., 1976; Cramer, et al., 1977). This loading method, generally referred to as remote loading, typically involves a drug having an ionizable amine group which is loaded by adding it to a suspension of liposomes prepared to have a lower inside/higher outside ion gradient, often a pH gradient.

However, there are recognized problems with remote loading, one being that not all ionizable drugs accumulate in the liposomes in response to an ion gradient (Chakrabarti, et al., 1995; Madden, et al., 1990). Another problem is that some agents which do accumulate in the liposomes are immediately released after accumulation. Yet another problem is that some agents which are successfully loaded and retained in the liposome in vitro have a high leakage rate from the liposomes in vivo, obviating the advantages of administering the agent in liposome-entrapped form.

SUMMARY OF THE INVENTION

In one aspect, the invention includes a composition for treatment of a bacterial infection. The composition includes liposomes composed of a vesicle-forming lipid and between 1–20 mole percent of a lipid derivatized with a hydrophilic polymer, and, entrapped within the liposomes, a drug-conjugate having anti-bacterial activity and composed of ciprofloxacin covalently attached to an amino acid. The amino acid is effective to enhance retention of the drug-conjugate in the liposomes relative to retention of ciprofloxacin in the liposomes.

In one embodiment, the amino acid is covalently attached to ciprofloxacin's piperazine ring.

In another embodiment, the amino acid is selected from alanine, valine, leucine, isoleucine, glycine, serine and threonine.

In another embodiment, the hydrophilic polymer in the liposome composition is polyethylene glycol having a molecular weight between 1,000–5,000 daltons.

In another aspect, the invention includes a method of preparing the liposome composition described above. The method includes preparing the liposomes to have an internal aqueous phase having a first ion concentration and incubating the liposomes in a bulk phase medium having a second ion concentration which is higher than said first ion concentration, the bulk phase medium including the drug-conjugate.

In one embodiment, the first lower ion concentration and said second higher ion concentration are hydrogen ion concentrations which define first and second pH values, respectively, where the first pH is between about 4.5–7.5 and is at least 2 pH units lower than the second pH of the external bulk phase medium.

In another embodiment, the liposomes are formed predominantly of lipids having phase transition temperatures above about 37° C., and the incubating is carried out at a temperature substantially above the phase transition temperatures of the liposome-forming lipids.

In another embodiment, the first and second pH values define a pH gradient which is due to a higher inside/lower outside ammonium ion gradient.

In another embodiment, the gradient is produced by an ammonium salt having a counterion which is effective to decrease the solubility of the drug-conjugate in the internal aqueous phase.

These and other objects and features of the invention will be more fully appreciated when the following detailed description of the invention is read in conjunction with the accompanying drawings.

DETAILED DESCRIPTION OF THE INVENTION

As discussed above, the present invention provides a liposome composition having a ciprofloxacin-amino acid conjugate entrapped therein. Section I below describes exemplary conjugates and their preparation and Section II describes preparation of liposomes and loading of the conjugate into liposomes. In Section III, liposomes containing two exemplary conjugates are characterized in vitro and in vivo.

I. Ciprofloxacin-Amino Acid Conjugate

Figure 1A:
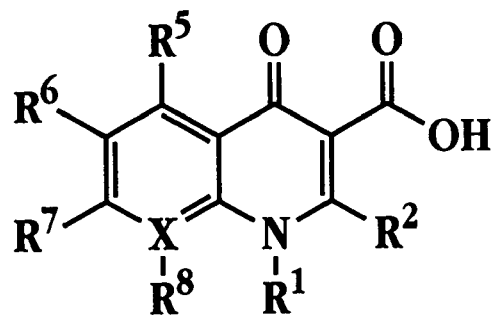
FIGS. 1A–1C show the structure of ciprofloxacin (FIG. 1A), the general structure for 6-fluoro-quinolones (FIG. 1B) and the general structure for quinolones (FIG. 1C)
Figure 1B:
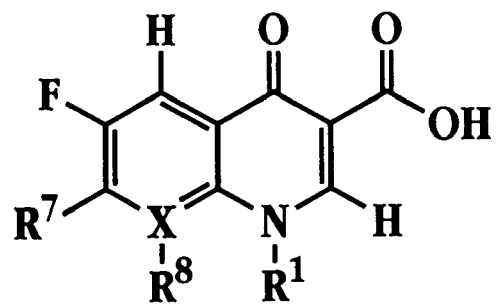
Figure 1C:
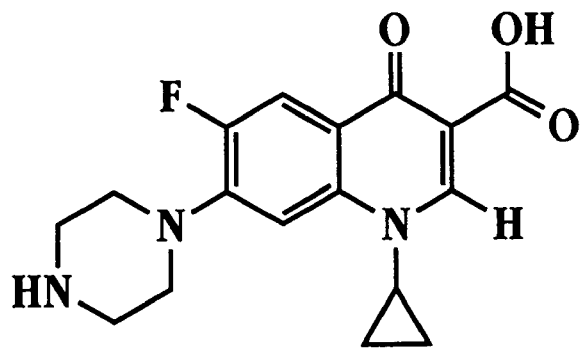

Ciprofloxacin, the structure of which is shown in FIG. 1A, is a 6-fluoro-quinolone, and more generally is of the class of antibacterial agents known as quinolones. The general structures for 6-fluoro-quinolones and quinolones are shown in FIGS. 1B-1C, respectively.

Ciprofloxacin, (1 -cyclopropyl-6-fluoro- 1,4-dihydro-4-oxo-7-( 1-piperazinyl)-3-quinoline carboxylic acid), is one of the more potent members of the quinolones. Like the other quinolones, ciprofloxacin acts by inhibiting bacterial DNA replication. The drug binds to the β-subunit of DNA gyrase, an essential enzyme for DNA replication that allows supercoils to be relaxed and reformed, and effectively inhibit its activity (Salyers, et al., 1994).

Ciprofloxacin, shown in FIG. 1A, includes a cyclopropyl ring at R1 and piperazine ring at R7, which includes an ionizable amine having a pKa of about 8.7. The drug is effective against most gram negative and some gram positive pathogenic bacteria. However, the therapeutic effectiveness of the antibacterial is limited by its short-elimination half-life of 4 hours, which makes it difficult to maintain a therapeutic concentration in the blood.

As described above, entrapment of drugs into liposomes is one approach to improving the therapeutic effectiveness of the drug, and entrapment of ciprofloxacin has been described (Ryan, et al., 1991; Wong, et al., 1995, Hope, et al., 1996). However, liposomally-entrapped ciprofloxacin is not retained in the liposomes for a time sufficient to achieve the extent of in vivo biodistribution of long-circulating liposomes having a surface-coating of hydrophilic polymer chains. This is demonstrated in Comparative Example 1, which describes preparation of liposomes having a surface coating of polyethylene glycol chains and entrapment of ciprofloxacin in the liposomes by remote loading. The ciprofloxacin-containing liposomes were tested in vitro to measure the amount of ciprofloxacin that was released from the liposomes in plasma (Comparative Example 1B). It was found that 85% of the drug leaked from the liposomes after incubation in plasma for 24 hours at 37° C., with 40% of the drug released within one hour.

Long-circulating liposomes remain in the blood stream for up to 24 hours. "Long-circulating" liposomes as used herein refers to liposomes having a surface coating of hydrophilic polymer chains, such as the polyethylene glycol-coated liposomes described in U.S. Pat. No. 5,013, 556. Up to 10% of the injected dose of long-circulating liposomes remains in the blood stream 24 hours after injection, in contrast to conventional liposomes, e.g., liposomes lacking the coating of polymer chains, which are cleared from the bloodstream in several hours. Thus, long-circulating liposomes achieve a biodistribution in the body that includes organs and tissues other than those of the mononuclear phagocyte system or reticuloendothelial system where conventional liposomes rapidly accumulate after administration (Paphadjopoulos, et al., 1991). Clearly, a ciprofloxacin-liposome composition which releases more than half of the load of ciprofloxacin in a period of several hours due to leakage of the drug across the liposome bilayer does not take advantage of the long-circulating lifetime and good biodistribution of long-circulating liposomes.

Applicants have found that ciprofloxacin when conjugated to an amino acid can be loaded into a liposome and is retained in the liposome significantly longer than ciprofloxacin. Thus, the invention provides a liposome composition including a ciprofloxacin conjugate which is able to take advantage of the long blood circulation lifetime to achieve good biodistribution and sustained release of the entrapped compound.

Figure 2:
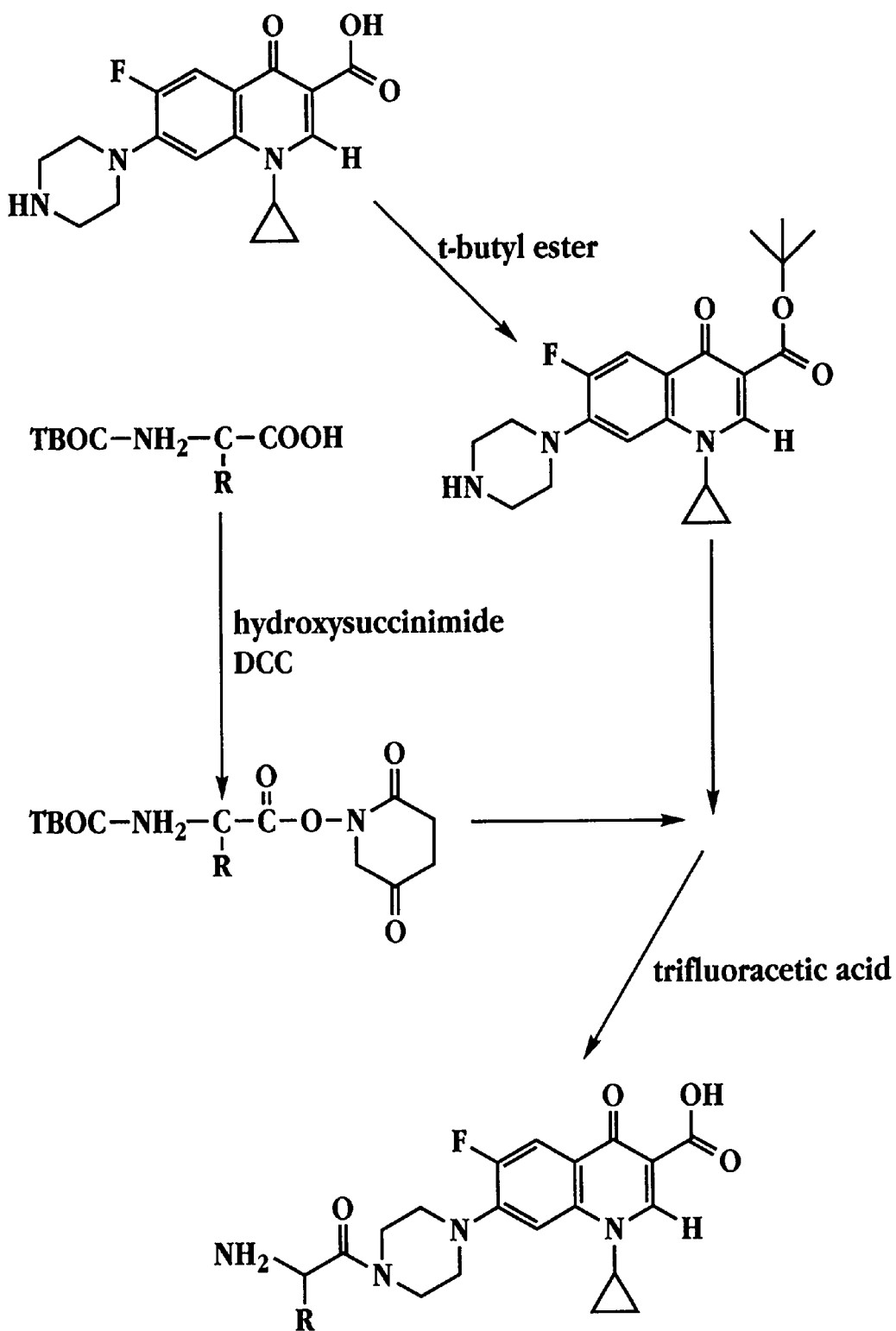
FIG. 2 is a general reaction scheme for preparation of an amino acid amide of ciprofloxacin.

A synthetic reaction scheme for preparation of ciprofloxacin-amino acid conjugates is illustrated in FIG. 2 and described in Example 2. In general, the 3-carboxy group of ciprofloxacin is protected by any of a number of carboxy protecting groups known in the art (Greene, et al., 1991), and a t-butyl ester is illustrated in FIG. 2. The protected-ciprofloxacin is then reacted with an N-protected basic amino acid in the presence of a condensing agent to conjugate the secondary amino group of the piperazine ring of ciprofloxacin to the alpha carboxyl group of the basic amino acid. The resulting protected amide conjugate is then deprotected prior to loading into liposomes. The amide linkage is chemically stable, however, it may be cleaved in vivo by lysozymes following the uptake of the liposomes by macrophages.

Figure 3A:
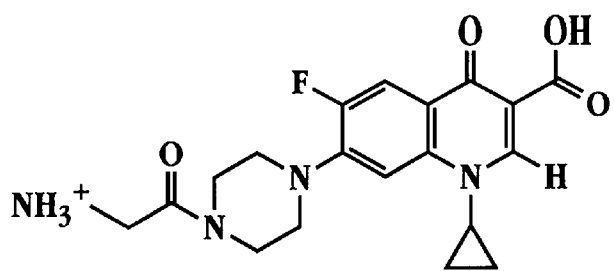
FIGS. 3A–3D show exemplary ciprofloxacin-amino acid conjugates prepared in support of the invention, including ciprofloxacin-glycine (FIG. 3A), ciprofloxacin-lysine (FIG. 3B), ciprofloxacin-threonine (FIG. 3C) and ciprofloxacin-leucine (FIG. 3D)
Figure 3B:
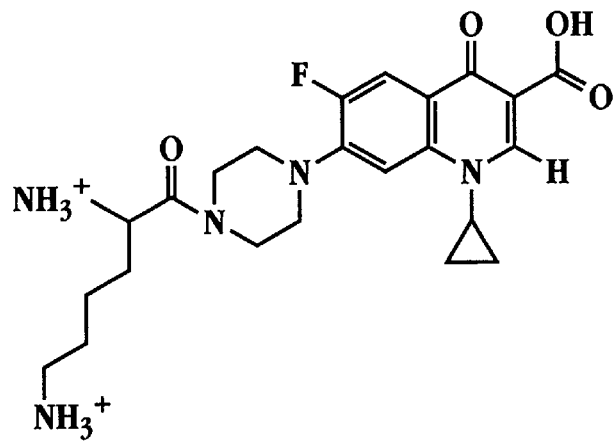
Figure 3C:
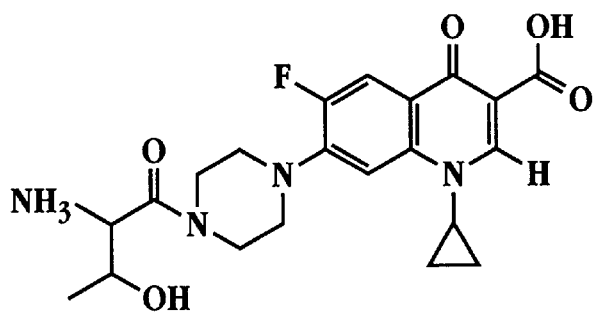
Figure 3D:
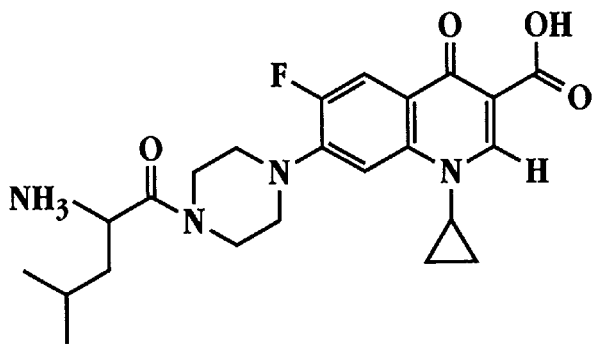

In studies in support of the invention, ciprofloxacin was conjugated according to the scheme of FIG. 2 to the following amino acids: glycine, lysine, threonine and leucine. The structures of these ciprofloxacin-amino acid conjugates are shown in FIGS. 3A–3D, where FIG. 3A shows ciprofloxacin-glycine, FIG. 3B shows ciprofloxacin-lysine, FIG. 3C shows ciprofloxacin-threonine and FIG. 3D shows ciprofloxacin-leucine. As will be described below, glycinyl-ciprofloxacin and lysinal-ciprofloxacin were entrapped in liposomes and tested for in vitro plasma leakage and for in vivo blood circulation lifetime.

More generally, the invention contemplates the use of any of the amino acids, so long as the conjugate retains an amount of antibacterial activity suitable for therapeutic efficacy when the conjugate is administered in liposome entrapped form. In one embodiment, preferred amino acids are those having a linear or branched aliphatic R group, such as alanine, valine, leucine, isoleucine glycine, serine, threonine, aspartic acid, glutamic acid, lysine and arginine. In another embodiment, amino acids having a pKa above 9.0 are preferred. For example, the pKa values associated with the $NH_3$ in glycine, alanine and leucine are 9.6, 9.7 and 9.6, respectively. Lysine and arginine are triprotic, having a second amino group in the R group. The pKa values for the amino groups in lysine are 8.95 and 10.53 and for arginine are 9.04 and 12.48 (Lehninger).

Figure 4A:
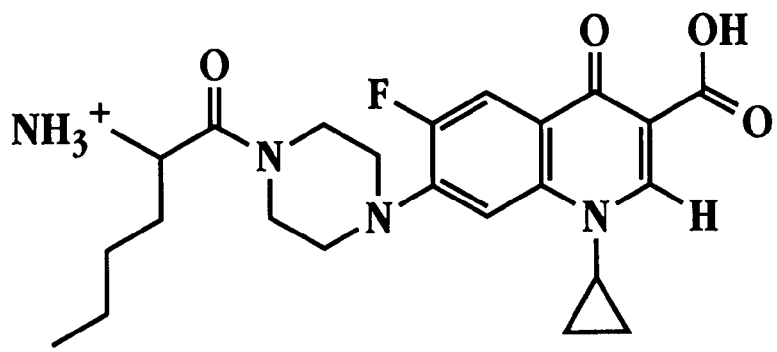
FIGS. 4A-4B show structures of α-aminocaproyl ciprofloxacin (FIG. 4A) and ε-aminocaproyl ciprofloxacin (FIG. 4B)
Figure 4B:
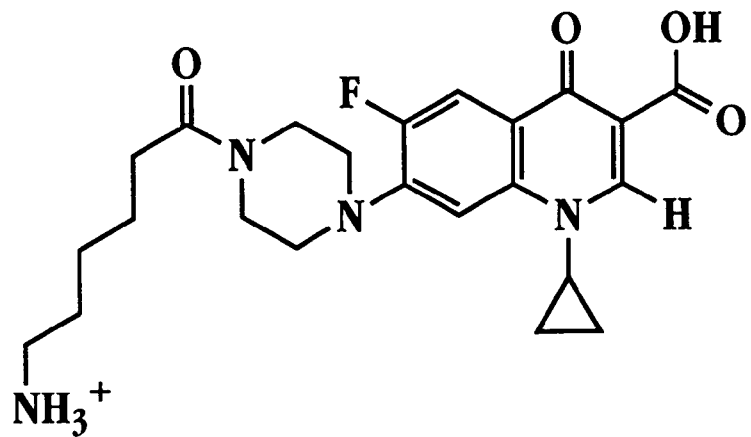
Figure 5A:
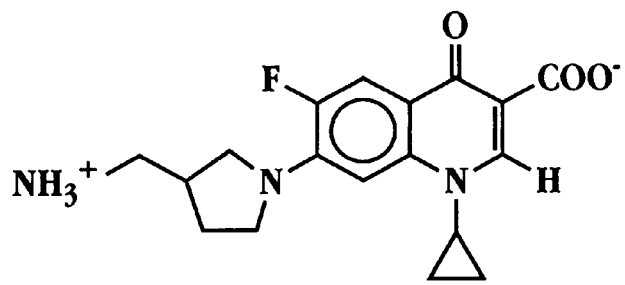
FIGS. 5A–5D show other 6-fluoro-quinolones suitable for use in the present invention.
Figure 5B:
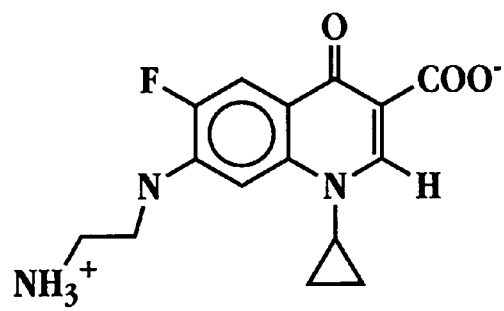
Figure 5C:
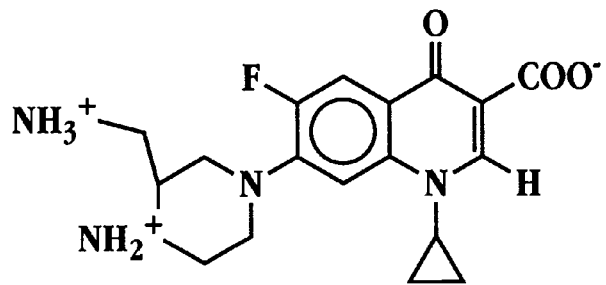
Figure 5D:
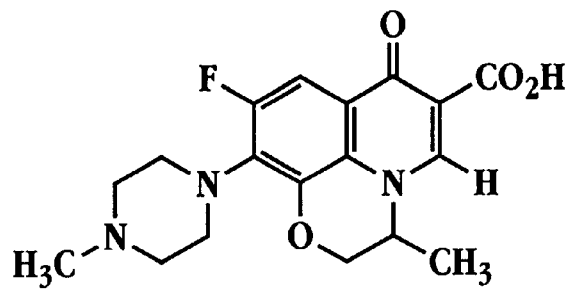

It will be appreciated that the general concept of the invention to provide a quinolone stably entrapped in a liposome and retained for a time sufficient for biodistribution according to the biodistribution of the liposomes, is applicable to ciprofloxacin modified with other ligands which provide enhanced liposome retention. For example, ciprofloxacin can be modified with α-aminocapric acid (pKa 9.6) and ε-aminocapric acid (pKa 10.5) to give α-aminocaproyl-ciprofloxacin (FIG. 4A) and ε-aminocaproyl-ciprofloxacin (FIG. 4B).

More generally, the invention contemplates use of any 6-fluoro-quinolone compound having the general structure shown in FIG. 1B. 6-fluoro-quinolones have been widely studied and many structural variations are known, many of which are suitable for use in the present invention. Generally, any 6-fluoro-quinolone having a pKa value of greater than about 9.0 is suitable for use, and it will be appreciated that the 6-fluoro-quinolone may include a moiety with a pKa greater than 9.0 or the existing compound may be modified, as described above, with an amino acid or other compound, to include a moiety with a pKa greater than 9.0.

With reference again to FIG. 1B, 6-fluoro-quinolones are typically where $R_1$ is a $C_1$ to $C_3$ alkyl group, such as methyl, ethyl, propyl, or cyclopropyl, which may be substituted at one or more positions with F, Cl, or Br; $R_7$ is a linear, branched or cyclic nitrogen-containing alkane which preferably contains an ionizable amino group; exemplary $R_7$ substituents include ring structures such as 1-azetidyl, 1-piperazinyl, 4-methyl-1-piperazinyl, 4-ethyl-1-piperazinyl, 2-piperazinyl, 1-pyrrolidyl, each of which may be substituted with an $NH_2$, $NHCH_3$, $N(CH_3)_2$, 2-aminoethyl, ethylaminomethyl, 1-pyrrolidyl, or aminoethylaminomethyl group, other exemplary saturated and unsaturated nitrogen heterocycles include monocyclic heterocycles, e.g. imidazole, imidazoline, dihydropyrrole, 1,2,3,6-tetrahydropyridine, 1,4,5,6-tetrahydropyrimidine, pyrrolidine, morpholine, piperidine, piperazine, 1,3,5-triazine and bicyclic heterocycles, e.g. perhydroindole, perhydroquinoline, perhydroisoquinoline, perhydro-7-azaindole, perhydro-4-azabenzimidazole, 1,5-diazabicyclo[4.3.0]nonene (DBN), 1,8-diazabicyclo[5.5.0]undec-7-ene (DBU), 1,5-diazabicyclo[4.3.0]nonane, 1,8-diazabicyclo[5.5.0]undecane, 1,4-diazabicyclo[2.2.2]octane (triethylenediamine), 3-azabicyclo[3.2.2]nonane, 3-azabicyclo[4.3.0]nonane, 3-azabicyclo[3.3.0]octane, 2,8-diazabicyclo[4.3.0]nonane, 5-diazabicyclo[4.3.0]nonane, 1,5,7-triazabicyclo[4.4.0]dec-5-ene, 2,7-diazaspiro[4.4]nonane; X is N or C, such that when X is N, $R_8$ is nothing, and when X is C, $R_8$ is H, F, Cl, or $CF_3$, $OCH_3$, or $OCH_2CH_3$, or $R_1$ and $R_8$ together comprise a two- or three-atom alkyl or alkoxy bridge linking the 1 and 8 ring atoms in the quinolone ring to form a five- or six-member ring, respectively. Where cis- and trans-stereoisomers are possible, both isomers are contemplated. When asymmetric chiral centers are present, the compound may include a single stereoisomer or a mixture, typically a racemic mixture, of stereoisomers.

Some exemplary 6-fluoro-quinolones contemplated for use in the present invention are shown in FIGS. 5A–5D.

Still more generally, the invention contemplates use of any compound in the class of quinolones, that is, any of the 4-pyridone-3-carboxylic acid antibacterials having the general structure shown in FIG. 1C, where X is N or C and $R_1$, $R_2$, $R_5$, $R_6$, $R_7$ and $R_8$ can be any group. Recent structure activity correlations have resulted in the synthesis of numerous quinolones having antibacterial activity (Culbertson, et al., 1990; Domagala, et al., 1986; Hagen, et al., 1990, 1991; Klopman, et al., 1993; Sanchez, et al., 1988) and synthesis of such compounds can be readily performed by one of skill in the art.

It will be appreciated that the general reaction of FIG. 2, discussed above, is suitable for attachment of any amino acid to a quinolone having a primary or secondary amino group. The reactive amino group may be coupled to the carboxylic acid function of a basic amino acid by an amide linkage.

II. Liposome Composition

The ciprofloxacin-amino acid conjugate described above is entrapped in liposomes, where "entrapped" refers to the compound being sequestered in the central aqueous compartment of the liposomes, in the aqueous space between liposome lipid bilayers, or within the bilayer itself. This section describes the preparation of liposomes for use in entrapping the drug-conjugate of the invention by remote loading.

A. Liposome Components

The liposomes of the invention are composed of vesicle-forming lipids, generally including amphipathic lipids having both hydrophobic tail groups and polar head groups. A characteristic of a vesicle-forming lipid is its ability to either (a) form spontaneously into bilayer vesicles in water, as exemplified by the phospholipids, or (b) be stably incorporated into lipid bilayers, by having the hydrophobic portion in contact with the interior, hydrophobic region of the bilayer membrane, and the polar head group oriented toward the exterior, polar surface of the membrane. A vesicle-forming lipid for use in the present invention is any conventional lipid possessing one of the characteristics described above.

The vesicle-forming lipids of this type are preferably those having two hydrocarbon tails or chains, typically acyl groups, and a polar head group. Included in this class are the phospholipids, such as phosphatidylcholine (PC), phosphatidylethanolamine (PE), phosphatidic acid (PA), phosphatidylglycerol (PG), and phosphatidylinositol (PI), where the two hydrocarbon chains are typically between about 14–22 carbon atoms in length, and have varying degrees of unsaturation. Preferred phospholipids include PE and PC. An exemplary PC is hydrogenated soy phosphatidylcholine (HSPC). Single chain lipids, such as sphingomyelin (SM) may also be used.

The above-described lipids and phospholipids whose acyl chains have a variety of degrees of saturation can be obtained commercially, or prepared according to published methods. Other lipids that can be included in the invention are glycolipids. The term "glycolipid" as used herein encompasses lipids having two hydrocarbon chains, one of which is the hydrocarbon chain of sphingosine, and one or more sugar residues.

Lipids for use in the present invention may be relatively "fluid" lipids, meaning that the lipid phase has a relatively low lipid melting temperature, e.g., at or below room temperature, or alternately, relatively "rigid" lipids, meaning that the lipid has a relatively high melting point, e.g., at temperatures up to 50° C. As a general rule, the more rigid, i.e., saturated lipids, contribute to greater membrane rigidity in the lipid bilayer structure, and thus to more stable drug retention after active drug loading. Preferred lipids of this type are those having phase transition temperatures above about 37° C.

The liposomes may additionally include lipids that can stabilize a vesicle or liposome composed predominantly of phospholipids. The most frequently employed lipid from this group is cholesterol at levels between 25 to 45 mole percent.

Liposomes used in the invention preferably contain between 30–75 percent phospholipids, preferably phosphatidylcholine (PC), 25–45 percent cholesterol, and 1–20 percent polymer-derivatized lipid, expressed on a molar percent basis. One exemplary liposome formulation contains 50 mole percent phosphatidylcholine and 45 mole percent cholesterol and 5 mole percent of a polymer-derivatized lipid, mPEG-DSPE, now to be described.

The liposomes of the invention include a surface coating of a hydrophilic polymer chain. "Surface-coating" refers to the coating of any hydrophilic polymer on the surface of liposomes. The hydrophilic polymer is included in the liposome by including in the liposome composition one or more vesicle-forming lipids derivatized with a hydrophilic polymer chain. The vesicle-forming lipids which can be used are any of those described above for the first vesicle-forming lipid component, however, vesicle-forming lipids with diacyl chains, such as phospholipids, are preferred. One preferred phospholipid is phosphatidylethanolamine (PE), which contains a reactive amino group convenient for coupling to the activated polymers. One exemplary PE is distearyl PE (DSPE).

A preferred hydrophilic polymer for use in coupling to a vesicle forming lipid is polyethyleneglycol (PEG), preferably as a PEG chain having a molecular weight between 1,000–10,000 daltons, more preferably between 1,000–5,000 daltons.

Other hydrophilic polymers which may be suitable include polylactic acid, polyglycolic acid, polyvinylpyrrolidone, polymethyloxazoline, polyethyloxazoline, polyhydroxypropyl methacrylamide, polymethacrylamide, polydimethylacrylamide, and derivatized celluloses, such as hydroxymethylcellulose or hydroxyethylcellulose.

Preparation of lipid-polymer conjugates containing these polymers attached to a suitable lipid, such as PE, have been described, for example in U.S. Pat. No. 5,395,619, which is expressly incorporated herein by reference, and by Zalipsky in STEALTH LIPOSOMES (1995). Typically, between about 1–20 mole percent of the polymer-derivatized lipid is included in the liposome-forming components during liposome formation.

The hydrophilic polymer chains provide a surface coating of hydrophilic chains sufficient to extend the blood circulation time of the liposomes in the absence of such a coating. The extent of enhancement of blood circulation time is several fold over that achieved in the absence of the polymer coating, as described in co-owned U.S. Pat. No. 5,013,556, which is expressly incorporated herein by reference.

Further, the liposomes may be prepared to contain surface groups, such as antibodies or antibody fragments, small effector molecules for interacting with cell-surface receptors, antigens, and other like compounds for achieving desired target-binding properties to specific cell populations. Here the lipid component included in the liposomes would include either a lipid derivatized with the targeting molecule, or a lipid having a polar-head chemical group that can be derivatized with the targeting molecule in preformed liposomes, according to known methods.

B. Preparing Ion Gradient Liposomes

As discussed above, liposomes with a high internal concentration of drug can be prepared by remote loading. In this technique, a drug is accumulated in the liposomes' central compartment in response to an ion gradient, typically a pH gradient across the liposome bilayer. Preparation of liposomes having a pH gradient and loading of a drug is described in this section.

Liposomes with the desired ion gradient may be prepared by a variety of techniques. In a typical procedure, a mixture of liposome-forming lipids is dissolved in a suitable organic solvent and evaporated in a vessel to form a thin film. The film is then covered with an aqueous medium containing the solute species that will form the aqueous phase in the liposome interior spaces, in the final liposome preparation, as discussed below. The lipid film hydrates to form multilamellar vesicles (MLVs), typically with heterogeneous sizes between about 0.1 to 10 microns.

After liposome formation, the vesicles may be sized to achieve a size distribution of liposomes within a selected range, according to known methods. The liposomes are preferably uniformly sized to a selected size range between 0.04 to 0.25 μm. Small unilamellar vesicles (SUVs), typically in the 0.04 to 0.08 μm range, can be prepared by extensive sonication or homogenization (Martin, et al., 1990) of the liposomes.

Homogeneously sized liposomes having sizes in a selected range between about 0.08 to 0.4 microns can be produced, e.g., by extrusion through polycarbonate membranes or other defined pore size membranes having selected uniform pore sizes ranging from 0.03 to 0.5 microns, typically, 0.05, 0.08, 0.1, or 0.2 microns. The pore size of the membrane corresponds roughly to the largest size of liposomes produced by extrusion through that membrane, particularly where the preparation is extruded two or more times through the same membrane.

The sizing is preferably carried out in the original lipid-hydrating buffer, so that the liposome interior spaces retain this medium throughout the initial liposome processing steps.

After sizing, the external medium of the liposomes is treated to produce an ion gradient across the liposome membrane, which is typically a lower inside/higher outside concentration gradient. This may be done in a variety of ways, e.g., by (i) diluting the external medium, (ii) dialysis against the desired final medium, (iii) molecular-sieve chromatography, e.g., using Sephadex G-50, against the desired medium, or (iv) high-speed centrifugation and resuspension of pelleted liposomes in the desired final medium.

The external medium which is selected will depend on the mechanism of gradient formation and the external pH desired, as will now be considered.

In the simplest approach for generating a pH gradient, the hydrated sized liposomes have a selected internal-medium pH. The suspension of the liposomes is titrated until a desired final pH is reached, or treated as above to exchange the external phase buffer with one having the desired external pH. For example, the original medium may have a pH of 5.5, in a selected buffer, e.g., glutamate or phosphate buffer, and the final external medium may have a pH of 8.5 in the same or different buffer. The internal and external media are preferably selected to contain about the same osmolarity, e.g., by suitable adjustment of the concentration of buffer, salt, or low molecular weight solute, such as sucrose.

In another general approach, the gradient is produced by including in the liposomes, a selected ionophore. To illustrate, liposomes prepared to contain valinomycin in the liposome bilayer are prepared in a potassium buffer, sized, then exchanged with a sodium buffer, creating a potassium inside/sodium outside gradient. Movement of potassium ions in an inside-to-outside direction in turn generates a lower inside/higher outside pH gradient, presumably due to movement of protons into the liposomes in response to the net electronegative charge across the liposome membranes (Deamer, et al., 1972).

In another more preferred approach, the proton gradient used for drug loading is produced by creating an ammonium ion gradient across the liposome membrane, as described, for example, in U.S. Pat. No. 5,192,549. Here the liposomes are prepared in an aqueous buffer containing an ammonium salt, typically 0.1 to 0.3 M ammonium salt, such as ammonium sulfate, at a suitable pH, e.g., 5.5 to 7.5. After liposome formation and sizing, the external medium is exchanged for one lacking ammonium ions, e.g., the same buffer but one in which ammonium sulfate is replaced by NaCl or a sugar that gives the same osmolarity inside and outside of the liposomes.

After liposome formation, the ammonium ions inside the liposomes are in equilibrium with ammonia and protons. Ammonia is able to penetrate the liposome bilayer and escape from the liposome interior. Escape of ammonia continuously shifts the equilibrium within the liposome toward the right, to production of protons.

The ammonium ion gradient provides a number of advantages in active drug loading over the other two approaches given above. Among these are:

i. The system is able to generate protons in response to drug loading, such that the ability to load drugs is not limited by the initial concentration of protons or initial pH gradient. That is, as drug molecules in non-protonated form are taken up and protonated within the liposomes, the loss of protons within the liposomes shifts the ammonium/ammonia equilibrium toward ammonia and protonproduction, maintaining the concentration of protons at a relatively constant level independent of amount of drug loaded. The only requirement is that the initial ammonium ion concentration within the liposomes is in substantial molar excess of the final loaded drug concentration.

ii. The system is able to act like a battery during liposome storage, replacing protons that may be lost by diffusion out of the membranes with newly produced protons, as the ammonium/ammonia equilibrium is shifted toward ammonia production.

iii. The counterion of the ammonium salt, e.g., sulfate counterion, may further enhance drug loading, by its ability to precipitate or form insoluble complexes with the drug being loaded.

C. Liposome Loading

The liposomes formed as above are used in loading the ciprofloxacin-amino acid compound of the invention. In this method, the compound is added to a suspension of the pH gradient liposomes, and the suspension is treated under conditions effective to allow passage of the compound from the external medium into the liposomes. Incubation conditions suitable for drug loading are those which (i) allow diffusion of the derivatized compound, with such in an uncharged form, into the liposomes, and (ii) preferably lead to high drug loading concentration, e.g., 50–200 mM drug encapsulated.

The loading is preferably carried out at a temperature above the phase transition temperature of the liposome lipids. Thus, for liposomes formed predominantly of saturated phospholipids, the loading temperature may be as high as 60° C. or more. The loading period is typically between 15–120 minutes, depending on permeability of the derivatized drug to the liposome bilayer membrane, temperature, and the relative concentrations of liposome lipid and drug.

Figure 6:
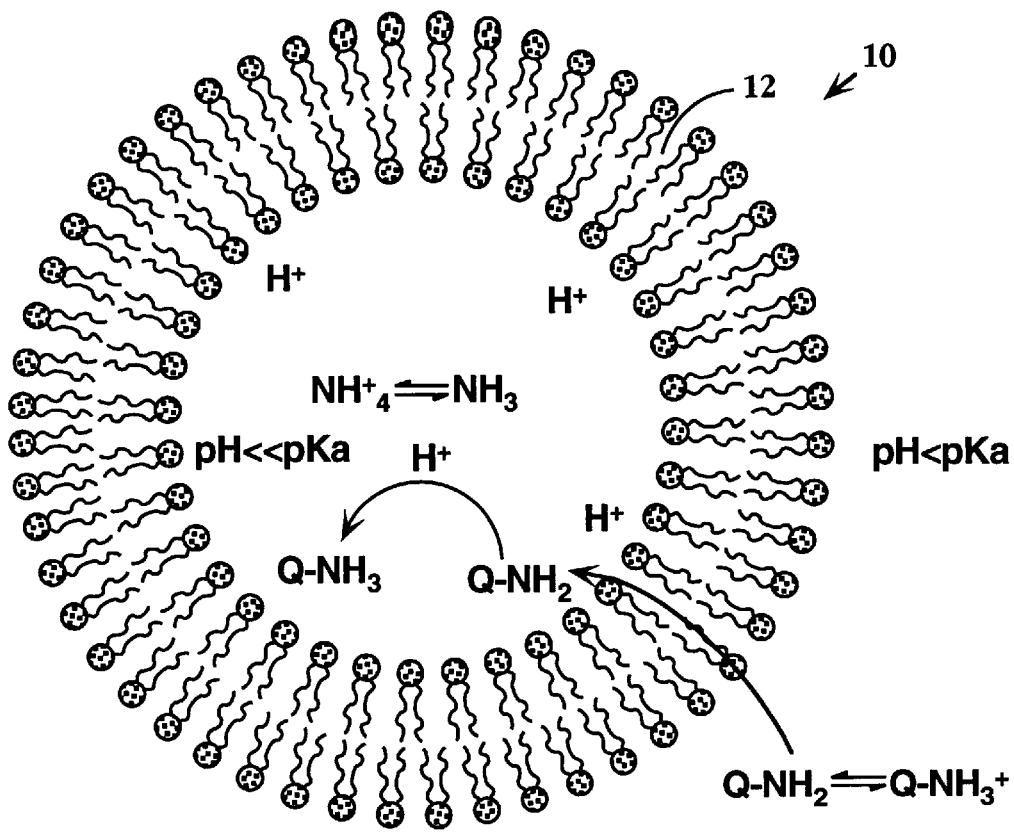
FIG. 6 illustrates the ionization events in loading the ciprofloxacin-amino acid conjugate into liposomes against an ion gradient.

FIG. 6 illustrates the mechanism of drug loading into liposomes having an ion gradient. The figures shows a liposome 10 having a bilayer membrane 12 and a lower inside/higher outside pH gradient by virtue of a higher inside/lower outside ammonium ion concentration.

In the external liposome environment, e.g., the liposome suspension medium or bulk phase medium, the drug-conjugate (designated Q-NH$_2$) is in equilibrium with its protonated amino form, the equilibrium balance being in accordance with the selected external pH. Typically, the internal pH is between 4.5–7.5 and is about 2 pH units lower than the external pH, which is typically between 6.5–9.5.

The neutral form of the drug can permeate the liposome bilayer under the incubation conditions during liposome loading, and the uncharged drug external the liposome is in equilibrium with the uncharged drug within the liposome interior. As the neutral drug permeates the liposome bilayer, it protonates in response to the excess of protons accumulated in the liposome interior. The protonated, charged form of the drug does not readily permeate across the liposome bilayer, thus, the drug accumulates in the liposomes.

It will be appreciated that the protonated form of the drug in the liposome interior can form a complex or precipitate with a counterion, such as sulfate counterion in an ammonium salt. In this case, the compound is further driven toward an entrapped state, increasing the concentration of compound that can be entrapped, and the stability of drug entrapment. The solubility of a derivatized compound in various ammonium-salt counterions can be determined by standard methods, for purposes of selecting a counterion which will lead to complex formation.

With proper selection of liposome concentration, external concentration of added compound, and the pH gradient, essentially all of the compound may be loaded into the liposomes. For example, with a pH gradient of 3 units (or the potential of such a gradient employing an ammonium ion gradient), the final internal:external concentration of drug will be about 1000:1. Knowing the calculated internal liposome volume, and the maximum concentration of loaded drug, one can then select an amount of drug in the external medium which leads to substantially complete loading into the liposomes.

Alternatively, if drug loading is not effective to substantially deplete the external medium of free drug, the liposome suspension may be treated, following drug loading, to remove non-encapsulated drug. Free drug can be removed, for example, by molecular sieve chromatography, dialysis, or centrifugation.

III. Characterization of the Liposome Composition

As described above, glycinyl-ciprofloxacin was prepared as set forth in Example 2A-2B and tested for antimicrobial activity in vitro, as described in Example 2C. The minimum inhibitory concentration of the drugs against the bacterial strains *S. pyrogenes, E. faecalis, S. aureus, E. coli* and *P. aeruginosa* were determined. The results are shown in Table 1 and are compared to ciprofloxacin.

TABLE 1

Activity of Ciprofloxacin and Glycinyl-ciprofloxacin

Minimum Inhibitory Concentration (µg/ml)

| Drug | S. pyrogenes | E. faecalis | S. aureus | E. coli | P. aeruginosa |
|---|---|---|---|---|---|
| cipro | <0.5 | 1.0 | 1.0 | <0.5 | <0.5 |
| G-cipro | 4 | 32 | 32 | 8 | >512 |

Derivatization of ciprofloxacin with glycine resulted in some loss of potency of the drug, as evidenced by the higher MICs of glycinyl-ciprofloxacin. However, the loss of potency would be offset by the better biodistribution offered by long-circulating liposomes and, therefore, a lower drug dose needed to provide equivalent efficacy.

As described in Example 2D, the in vitro plasma leakage of liposome-entrapped glycinyl-ciprofloxacin and lysinyl-ciprofloxacin were determined. Briefly, liposomes containing glycinyl-ciprofloxacin or lysinyl-ciprofloxacin were incubated in rat plasma for 24 hours at 37° C. At the end of the 24 hour incubation period, the plasma was analyzed for the presence of free drug. No free drug was detected in the plasma for either the liposome entrapped lysinyl-ciprofloxacin or the liposome-entrapped glycinyl-ciprofloxacin. The percent recovery of drug from the liposomal fractions was 93% for the liposome entrapped lysinyl-ciprofloxacin and 100% for the liposome-entrapped glycinyl-ciprofloxacin.

In contrast, and as discussed above with respect to Comparative Example 1, neat ciprofloxacin leaked from the liposomes with 85% of the drug recovered in the plasma after the 24 hour incubation period. Clearly, the amino acid modification to ciprofloxacin is effective to enhance retention of the drug in liposomes.

Figure 7:
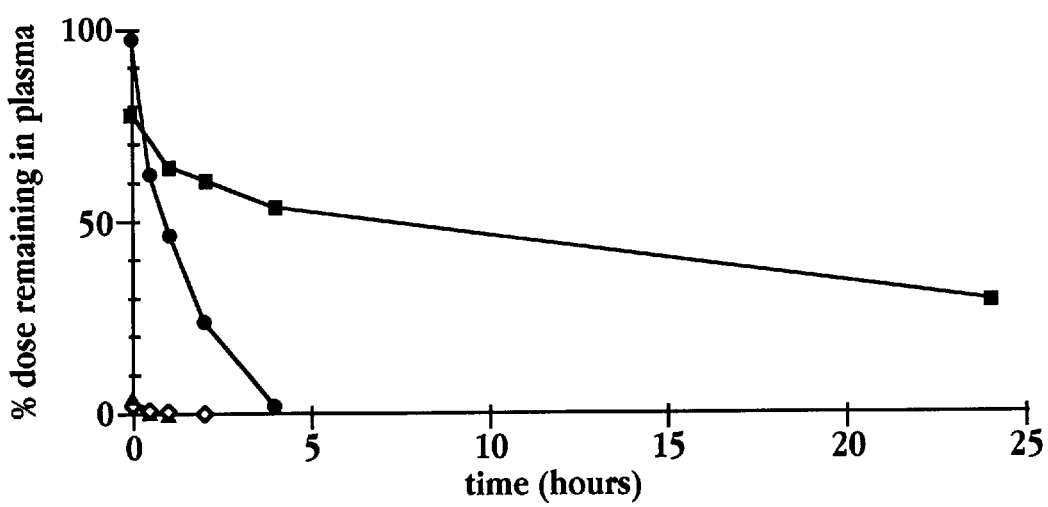
FIG. 7 is a plot showing percentage of drug remaining in the plasma after dosing rats with liposomally-entrapped glycinyl-ciprofloxacin (■), iposomally-entrapped ciprofloxacin (●) and free glycinyl-ciprofloxacin (◇) and free ciprofloxacin (▲).

The in vivo blood circulation lifetime of liposome-entrapped glycinyl-ciprofloxacin was determined in rats and compared to that of liposome-entrapped ciprofloxacin and free glycinyl-ciprofloxacin and free ciprofloxacin. As described in Example 2E, sixteen rats were divided into four test groups, and the four animals in each group received an intravenous bolus injection containing 30 µM/kg drug in one of the aforementioned formulations. The drug concentration in the plasma was determined as a function of time and the results are shown in FIG. 7.

As seen in the figure, the percentage of drug remaining in the plasma after dosing with liposomally entrapped glycinyl-ciprofloxacin (■) is significantly greater than the percentage of drug in the plasma after dosing with liposomally entrapped ciprofloxacin (●). After 24 hours, greater than 30% of the drug dose remains in the blood when administered as liposomally-entrapped glycinyl-ciprofloxacin. In contrast, for liposome-entrapped ciprofloxacin, after 4 hours, nearly all of the drug was cleared from the blood. Both free glycinyl-ciprofloxacin (◇) and free ciprofloxacin (▲) were cleared from the blood in less than 1 hour.

The plasma half life of glycinyl-ciprofloxacin entrapped in liposomes having a surface-coating of PEG was determined to be about 24 hours. This is approximately equivalent to the liposomes themselves, an indication that the drug is retained in the liposomes in vivo. This is further supported by the fact that free glycinyl-ciprofloxacin is cleared from the blood in about 30 minutes. In contrast, ciprofloxacin entrapped in liposomes having a surface coating of PEG had a blood circulation half life of approximately 1 hour. Free ciprofloxacin is cleared in about 30 minutes. In this case, while the liposomes are able to remain in circulation for as long as 24 hours, the ciprofloxacin is cleared more rapidly, indicating that the drug is leaking out of the liposomes in vivo.

These observations are evidence that by modifying a quinolone appropriately, for example by increasing the amine strength of the quinolone through derivatization with an amino acid or through careful selection of an existing quinolone having the requisite pKa value, or by synthesizing a new quinolone drug or analog, it is possible to improve the retention of the drug in liposome.

It will further be appreciated that the pKa value of the quinolone may work in conjunction with other features of a selected quinolone to enhance retention in a liposomes, for example, the compound's solubility and diffusivity coefficients.

The liposome composition of the invention can be used in the treatment of a variety of bacterial infections, including treatment of Mycobacterium infection, particularly *Mycobacterium tuberculosis, M. kansasil, M. Xenopi, M. fortuitum*, and *M. avium-M. intracellular* complex.

Other conditions treatable with a liposome-entrapped quinolone compound include chronic skin infections, such as decubitus ulcers or bedsores. Administration in a liposome-entrapped form offers the advantage of that the long circulation time of the liposomes allows the drug-carrying liposomes to accumulate at the site of infection and inflammation.

Multiple drug resistant tuberculosis is another condition treated with quinolone agents and which would benefit from administration in a liposome-entrapped form. This is because tuberculosis often resides in macrophages which actively take up PEG-coated liposomes, resulting in a concentration of the drug at the infection site.

Other conditions include pulmonary infections caused by gram-negative Pseudomonas, chronic bone infections and conditions related to macrophage dwelling mycobacterium.

IV. Examples

The following comparative example and example illustrate preparation of liposomes, preparation of ciprofloxacin-amino acid conjugates and loading of the conjugate into the liposomes. The examples are in no way intended to limit the scope of the invention.

Comparative Example 1

Preparation and Characterization of Liposomes Containing Ciprofloxacin

A. Liposome Preparation and Loading

Liposome having a surface-coating of polyethylene glycol were prepared by dissolving 661.1 mg hydrogenated soy phosphatidylcholine (HSPC), 220.5 mg cholesterol and 220.5 mg of polyethylene glycol derivatized to disteroyl phosphatidylethanolamine (PEG-DSPE) in 10 ml chloroform in a 250 mL round bottom flask. The chloroform was removed using a flash evaporator under reduced pressure until dryness. To the thin lipid film on the surface of the flask was added 15 ml of a solution of 250 mM ammonium sulfate, pH 5.5 and the lipids were dispersed in the solution by vigorous shaking for approximately 30 minutes at 60° C. The multilamellar vesicles obtained were extruded 6 times through a 0.4 $\mu$m pore-size Nucleopore polycarbonate filter, 6 times through a 0.1 $\mu$m polycarbonate filter and 3 times through a 0.05 $\mu$m polycarbonate filter using a stainless steel extrusion cell under a pressure of 200–400 psig. The extrusion process was carried out at 60° C. Liposomes after the extrusion process had a mean-diameter of 100±30 nm. The liposomes were then dialyzed overnight against 4 liters 10% sucrose to remove external ammonium sulfate at 4° C.

A stock solution of ciprofloxacin at 40 mg/ml was prepared by dissolving ciprofloxacin HCl powder in a 10% sucrose aqueous solution. Active drug loading was carried out by mixing an equal volume of the liposomes prepared as described above at a total lipid concentration of 80 mg/ml with ciprofloxacin solutions at 40, 20, 10 or 5 mg/ml. The mixtures were incubated at 60° C. for 30 minutes. After incubation, the mixtures were immediately cooled in an ice bath. Aliquot samples were taken and the percent of drug loading was determined by using a Sephadex G-50 column (1.0×19 cm). The percent of drug loading for the liposome formulations having lipid/drug ratios of 2, 4, 8 and 16 were 49%, 75%, 90% and 91% respectively.

B. In vitro Release of Ciprofloxacin into Plasma

The liposome formulation having a lipid/drug ratio of 8 and a ciprofloxacin loading of 75% (approximately 75 mg/ml in liposome) was diluted 1/50 with rat plasma and incubated at 37° C. for 24 hours. At the end of incubation, 0.5 ml of the plasma was loaded on a Sepharose CL-4B column. Approximately 45 1-ml fractions were collected, and the liposomal and free drug fractions were pooled. The pooled fractions were extracted using a methanol and 1 N HCl solvent (9:1 v/v) in a 1:4 dilution. These were subsequently centrifuged to spin down the precipitated plasma proteins, and the supernatants analyzed via reverse phase HPLC using a C-19 column. The HPLC mobile phase was 85% 25 mM sodium phosphate buffer, pH 2.3 and 15% acetonitrile.

The percent of ciprofloxacin that leaked out of the liposomes in 24 hours was 85%.

Example 2

Preparation of Glycinyl-ciprofloxacin and Lysinyl-ciprofloxacin

A. Synthesis of Glycinyl-ciprofloxacin and Lysinyl-ciprofloxacin

N-TBOC protected amino acids were purchased commercially. The compounds were reacted with an equi-molar amount of N-hydroxysuccinimide and a 10% excess of dicyclohexylcarbodiimide (DCC) in methylene chloride to form the N-hydroxysuccinimide ester.

The esters were treated with 2 moles of triethylamine and 1 mole of dry carboxyl-protected ciprofloxacin HCl in a dry solvent to form the TBOC protected ciprofloxacin amide of the amino acid.

The ciprofloxacin-amides were deprotected with trifluoroacetic acid and then isolated by a method appropriate to the physical and chemical properties of the product. For example, L-threonine-ciprofloxacin was recovered by adjusting the pH of the aqueous suspension to pH 7 to cause separation of the crystalline conjugate. The conjugate of L-leurine-ciprofloxacin was recovered by 1-butanol extraction from a pH 7–8 aqueous solution followed by recrystallization from methanol. The derivative of L-lysine-ciprofloxacin was converted to a phosphotungstate by treatment with phosphotungstic acid and barium hydroxide and then converted to its sulfate by treatment with dilute sulfuric acid.

The identity of the recovered products were confirmed using proton NMR spectroscopy.

B. Liposome Preparation and Loading

Liposomes were prepared as described above in Comparative Example 1 by dissolving 585 mg hydrogenated soy phosphatidylcholine (HSPC), 261 mg cholesterol and 210 mg of PEG-DSPE (prepared as described, for example, in Zalipsky (1995) to form liposomes with the following composition: 50% HSPC, 45% cholesterol and 5% mPEG-DSPE.

Ciprofloxacin-glycine and ciprofloxacin-lysine drug conjugates were loaded into the liposomes via remote loading, as described above, at the following concentrations.

| Drug Conjugate | Drug:Lipid Ratio (mg/ml/mM) | Drug Conc. at Lipid Conc. of 36 mg/ml | % Loading | Internal Liposome Drug Conc. (mg/ml) |
|---|---|---|---|---|
| lysine-cipro | 2.5:50 | 1.825 | 73 | 13.1 |
| glycine-cipro | 5:50 | 5 | 75 | 37.5 |

C. Antimicrobial Activity

Antimicrobial activity of ciprofloxacin, glycinyl-ciprofloxacin and lysinal-ciprofloxacin were measured against S. pyrogenes, E. faecalis, S. aureus, E. coli and P. aeruginosa. Minimum inhibitory concentrations were determined by a broth microdilution technique following the National Committee for Clinical Laboratory Standards guidelines (NCCLS document M7-A, National Committee for Laboratory Standards, Villanova, Pa., 1994 Approved Standard for "Methods for dilution antimicrobial susceptibility tests for bacteria that grow aerobically") with a starting inoculum of 5×10$^5$ CFU/ml. The results for ciprofloxacin and glycinyl-ciprofloxacin are shown in Table 1.

D. In vitro Plasma Leakage Rate

The liposomes containing lysinyl-ciprofloxacin and glycinyl-ciprofloxacin were diluted $^1\!/_{10}$ and $^1\!/_{100}$, respectively, with rat plasma and incubated at 37° C. for 24 hours. The leakage of the drug-conjugates was measured by the method set forth in Comparative Example 1B above. At the end of the 24 hour incubation period, no free drug was detected in the plasma for either the liposome entrapped lysinyl-ciprofloxacin or the liposome-entrapped glycinyl-ciprofloxacin. The percent recovery of drug from the liposomal fractions was 93% for the liposome entrapped lysinyl-ciprofloxacin and 100% for the liposome-entrapped glycinyl-ciprofloxacin.

E. In vivo Blood Circulation Lifetime

Plasma residence time of liposome-entrapped glycinyl-ciprofloxacin and liposome-entrapped ciprofloxacin were determined in rats. Sixteen rats were divided into four test groups, and the four animals in each group received 30 $\mu$M/kg drug in a single intravenous bolus injection of liposome-entrapped glycinyl-ciprofloxacin or liposome-entrapped ciprofloxacin or free glycinyl-ciprofloxacin or free ciprofloxacin.

Blood samples were taken from the tail vein and the drug concentration in the plasma was determined by methanol extraction followed by HPLC analysis. The results are shown in FIG. 7.

Although the invention has been described with respect to particular embodiments, it will be apparent to those skilled in the art that various changes and modifications can be made without departing from the invention.

It is claimed:

1. A composition for treatment of a bacterial infection, comprising liposomes composed of a vesicle-forming lipid and between 1–20 mole percent of a lipid derivatized with a hydrophilic polymer, and entrapped within the liposomes, a drug-conjugate having anti-bacterial activity, said drug conjugate composed of ciprofloxacin covalently attached to an amino acid, said amino acid being effective to enhance retention of the drug-conjugate in the liposomes relative to retention of ciprofloxacin in the liposomes.

2. The composition of claim 1, wherein said amino acid is covalently attached to ciprofloxacin's piperazine ring.

3. The composition of claim 1, wherein said amino acid is selected from alanine, valine, leucine, isoleucine, glycine, serine and threonine.

4. The composition of claim 3, wherein said amino acid is glycine.

5. The composition of claim 1, wherein said hydrophilic polymer is polyethylene glycol having a molecular weight between 1,000–5,000 daltons.

6. A method of preparing the liposome composition of claim 1, comprising preparing liposomes to have an internal aqueous phase having a first ion concentration; and incubating the liposomes in a bulk phase medium having a second ion concentration which is higher than said first ion concentration, said bulk phase medium comprising said drug-conjugate.

7. The method of claim 6, wherein said first lower ion concentration and said second higher ion concentration are hydrogen ion concentrations which define first and second pH values, respectively, where the first pH is between about 4.5–7.5 and is at least 2 pH units lower than the second pH of the external bulk phase medium.

8. The method of claim 6, wherein the liposomes are formed predominantly of vesicle-forming lipids having phase transition temperatures above about 37° C., and said incubating is carried out at a temperature substantially above the phase transition temperatures of the liposome-forming lipids.

9. The method of claim 7, wherein said first and second pH values define a pH gradient which is due to a higher inside/lower outside ammonium ion gradient.

10. The method of claim 9, wherein said gradient is produced by an ammonium salt having a counterion which is effective to decrease the solubility of the drug-conjugate in the internal aqueous phase.

* * * * *

UNITED STATES PATENT AND TRADEMARK OFFICE
CERTIFICATE OF CORRECTION

PATENT NO.    : 5,972,379                                Page 1 of 1
DATED         : October 26, 1999
INVENTOR(S)   : Luke S.S. Guo et al.

It is certified that error appears in the above-identified patent and that said Letters Patent is hereby corrected as shown below:

<u>Drawings,</u>
Figure 1A, please replace the structure with the following structure:

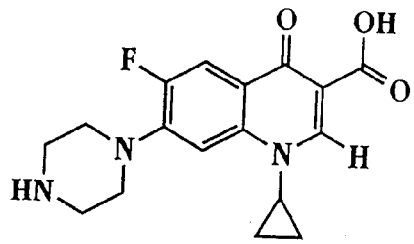

Figure 1C, please replace the structure with the following structure:

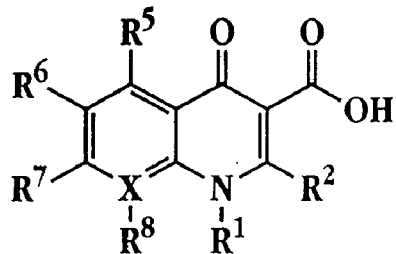

Signed and Sealed this

Twenty-third Day of December, 2003

JAMES E. ROGAN
*Director of the United States Patent and Trademark Office*